US008664593B2

(12) United States Patent
Prasad et al.

(10) Patent No.: US 8,664,593 B2
(45) Date of Patent: Mar. 4, 2014

(54) CONTROL OF GAS FLOW IN HIGH FIELD ASYMMETRIC WAVEFORM ION MOBILITY SPECTROMETRY

(71) Applicants: Satendra Prasad, San Jose, CA (US); Michael W. Belford, Los Altos, CA (US); Jean Jacques Dunyach, San Jose, CA (US)

(72) Inventors: Satendra Prasad, San Jose, CA (US); Michael W. Belford, Los Altos, CA (US); Jean Jacques Dunyach, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 13/787,574

(22) Filed: Mar. 6, 2013

(65) Prior Publication Data

US 2013/0306860 A1    Nov. 21, 2013

Related U.S. Application Data

(60) Provisional application No. 61/648,940, filed on May 18, 2012.

(51) Int. Cl.
*H01J 49/00* (2006.01)
*H01J 49/40* (2006.01)
*B01D 59/44* (2006.01)

(52) U.S. Cl.
USPC ........... 250/290; 250/281; 250/287; 250/288; 250/291

(58) Field of Classification Search
USPC .......................... 250/290, 281, 288, 287, 291
See application file for complete search history.

(56) References Cited

U.S. PATENT DOCUMENTS

| | | | |
|---|---|---|---|
| 6,713,758 B2 * | 3/2004 | Guevremont et al. | 250/290 |
| 6,806,466 B2 | 10/2004 | Guevremont et al. | |
| 7,034,289 B2 | 4/2006 | Guevremont et al. | |
| 7,223,967 B2 * | 5/2007 | Guevremont et al. | 250/288 |
| 7,638,765 B1 * | 12/2009 | Belford et al. | 250/290 |
| 8,158,932 B2 * | 4/2012 | Belford et al. | 250/287 |
| 2008/0067366 A1 | 3/2008 | Belford | |
| 2008/0315085 A1 | 12/2008 | Belford et al. | |
| 2010/0148053 A1 | 6/2010 | Belford et al. | |
| 2011/0253890 A1 | 10/2011 | Belford et al. | |

OTHER PUBLICATIONS

Australian Patent Office, "International Search Report for PCT/US2013/039516, dated Aug. 5, 2013."
Australian Patent Office, "Written Opinion of the International Searching Authority for PCT/US2013/039516, dated Aug. 5, 2013."
Prasad et al., "Control of Gas Flow in High Field Asymmetric Waveform Mobility Spectrometry, PCT/US2013/039516, filed May 3, 2013."

* cited by examiner

*Primary Examiner* — Nikita Wells
(74) *Attorney, Agent, or Firm* — Thomas F. Cooney (57) ABSTRACT

A High Field Asymmetric Waveform Ion Mobility Spectrometry (FAIMS) apparatus comprises (a) a first and a second gas inlet; (b) an expansion chamber receiving ions from an ion source and the first and second gas flows from the first and second gas inlets, respectively; (c) an outer electrode having a generally concave inner surface and comprising: (i) an ion inlet operable to receive, from the expansion chamber, the ions and a combined gas flow comprising portions of the first and second gas flows; and (ii) an ion outlet; and (d) an inner electrode having a generally convex outer surface that is disposed in a spaced-apart and facing arrangement relative to the inner surface of the outer electrode for defining an ion separation region therebetween, wherein the combined gas flow and a portion of the ions travel through the ion separation region from the ion inlet to the ion outlet.

15 Claims, 10 Drawing Sheets

CONTROL OF GAS FLOW IN HIGH FIELD ASYMMETRIC WAVEFORM ION MOBILITY SPECTROMETRY

CROSS REFERENCE TO RELATED APPLICATIONS

This application claims priority to and the benefit of the filing date, under 35 U.S.C. 119(e), of U.S. Provisional Application for Patent No. 61/648,940, filed on May 18, 2012 and titled "Control of Gas Flow in High Field Asymmetric Waveform Ion Mobility Spectrometry", said Provisional application assigned to the assignee of the present invention and incorporated herein by reference in its entirety.

FIELD OF THE INVENTION

The present invention relates generally to guiding ions in the presence of a gas and, more particularly, to simultaneously controlling the flow of gas and the flow of ions in field-asymmetric ion mobility spectrometers and mass spectrometers.

BACKGROUND OF THE INVENTION

In ion mobility spectrometry devices, separation of gas-phase ions is accomplished by exploiting variations in ion drift velocities under an applied electric field arising from differences in ion mobility. One well-known type of ion mobility spectrometry device is the High Field Asymmetric Waveform Ion Mobility Spectrometry (FAIMS) cell, also known by the term Differential Ion Mobility Spectrometry (DMS) cell, which separates ions on the basis of a difference in the mobility of an ion at high field strength (commonly denoted as $K_h$) relative to the mobility of the ion at low field strength (commonly denoted as K). Briefly described, a FAIMS cell comprises a pair of spaced apart electrodes that define therebetween a separation region through which a stream of ions is directed. An asymmetric waveform comprising a high voltage component and a lower voltage component of opposite polarity, together with a DC voltage (referred to as the compensation voltage, or CV) is applied to one of the electrodes. When the ion stream contains several species of ions, only one ion species is selectively transmitted through the FAIMS cell for a given combination of asymmetric waveform peak voltage (referred to as the dispersion voltage, or DV) and CV. The remaining species of ions drift toward one of the electrode surfaces and are neutralized. The FAIMS cell may be operated in single ion detection mode, wherein the DV and CV are maintained at constant values, or alternatively the applied CV may be scanned with time to sequentially transmit ion species having different mobilities. FAIMS cells may be used for a variety of purposes, including providing separation or filtering of an ion stream prior to entry into a mass analyzer.

Figure 1:
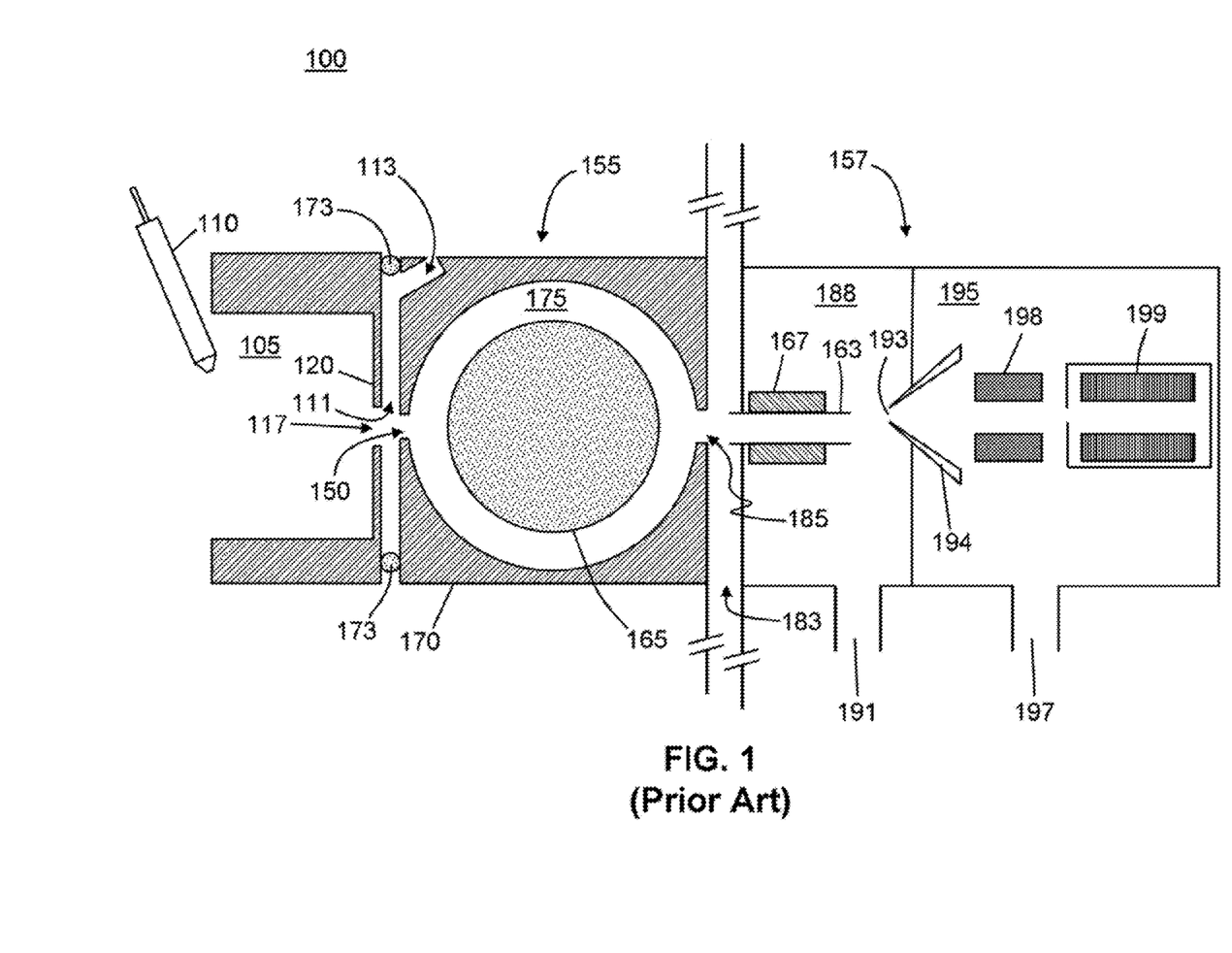
FIG. 1 is a schematic diagram depicting a first known system for analyzing ions including an ion mobility device.

FIG. 1 schematically depicts a first known system 100 for analyzing ions that includes a FAIMS device 155. A solution of sample to be analyzed is introduced as a spray of liquid droplets into an ionization chamber 105 via atmospheric pressure ion source 110. Ionization chamber 105 is maintained at a high pressure relative to the regions downstream in the ion path, typically at or near atmospheric pressure. Atmospheric pressure ion source 110 may be configured as an electrospray ionization (ESI) probe, wherein a high DC voltage (either positive or negative) is applied to the capillary or "needle" through which the sample solution flows. Other suitable ionization techniques may be utilized in place of ESI, including without limitation such well-known techniques as atmospheric pressure chemical ionization (APCI), heated electrospray ionization (HESI), and thermospray ionization.

Ions produced by the ion source enter the FAIMS cell 155 through an aperture 117 in an entrance plate 120 and then through an inlet orifice 150 after passing through an expansion chamber 111. The expansion chamber is provided with a gas, typically helium or other inert gas, which is introduced into the expansion chamber 111 via a gas conduit 113. A portion of the gas flows back into the ionization chamber 105 through entrance plate aperture 117 in counter-flow to the ions and droplets and serves to desolvate charged droplets. Another portion of the gas combines with the analyte ions in chamber 111 and serves as a carrier gas through the FAIMS cell 155. The combined ion/carrier gas flow then enters FAIMS cell 155 through inlet orifice 150. The carrier gas flow may be carefully metered to maintain flow rates within predetermined limits which will depend on the FAIMS cell size, electrode geometry, and operational considerations. An electrical potential difference is maintained between the entrance plate 120 and the FAIMS cell 155 and, thus, physical separation is maintained between these components. Accordingly, a non-conducting sealing element 173, such as a gasket or O-ring maintains the FAIMS gas within the apparatus and prevents contamination of this gas from outside air. Because of drawing-space limitations, this sealing element is not explicitly shown in some of the accompanying drawings.

Generally speaking, the FAIMS cell 155 includes inner and outer electrodes 165 and 170 having radially opposed surfaces, which define therebetween an annular separation region 175 (an "analytical gap") through which the ions are transported. The FAIMS cell geometry depicted in FIG. 1, as well as in other figures herein may be generally referred to as a "side-to-side FAIMS cell", in which the longitudinal axes (axes of cylindrical surfaces, directed out of the page) of inner electrode 165 and outer electrode 170 are oriented transversely with respect to the overall direction of ion flow. The principles of the design and operation of FAIMS cells and other ion mobility spectrometry devices have been extensively described elsewhere in the art (see, for example, U.S. Pat. No. 6,639,212 to Guevremont et al., incorporated by reference herein in its entirety), and hence will not be described in detail herein. In brief, the carrier gas and ions flow through the separation region 175 from inlet orifice 150 to exit orifice 185. Ion separation is effected within the separation region (analytical gap) 175 of the FAIMS cell 155 by applying an asymmetric waveform having a peak voltage (DV) and a compensation voltage (CV) to one of the inner or outer electrodes, 165, 170. The values of CV and DV are set to allow transmission of a selected ion species through separation region 175. Other ion species having different relative values of high field and low field mobilities will migrate to the surface of one of the electrodes and be neutralized.

Still referring to FIG. 1, the selected ions emerge from the FAIMS cell 155 through exit orifice 185 and pass through a small gap 183 separating the FAIMS cell 155 from a mass spectrometer 157. Whereas most of the carrier gas exhausts through the gap 183 at atmospheric pressure, ions are electrostatically guided into at least one reduced pressure chamber 188 of the mass spectrometer 157 through an orifice in the mass spectrometer or through an ion transfer tube 163. The at least one reduced pressure chamber may be evacuated by a vacuum port 191. At least a portion of ion transfer tube 163 may be surrounded by and in good thermal contact with a heat source, such as heater jacket 167. The heater jacket 167, which may take the form of a conventional resistance heater, is operable to raise the temperature of ion transfer tube 163 to promote further desolvation of droplets entering the ion transfer tube 163.

From the at least one reduced pressure chamber 188, ions are transferred through an orifice 193 of a skimmer 194 into a high vacuum chamber 195 maintained at a low pressure (typically around 100 millitorr) relative to the reduced pressure chamber 188. The high vacuum chamber 195 is typically evacuated by turbo or similar high-vacuum pumps via a vacuum port 197. The skimmer 194 may be fabricated from an electrically conductive material, and an offset voltage may be applied to skimmer 194 to assist in the transport of ions through interface region and into skimmer orifice 193. Ions passing through skimmer orifice 193 may be focused or guided through ion optical assembly 198, which may include various electrodes forming ion lenses, ion guides, ion gates, quadrupole or octopole rod sets, etc. The ion optical assembly 198 may serve to transport ions to an analyzer 199 for mass analysis. Analyzer 199 may be implemented as any one or a combination of conventional mass analyzers, including (without limitation) a quadrupole mass analyzer, ion trap, or time-of-flight analyzer.

Computational and experimental studies have shown that the gas stream carrying ions from the ion source enters the FAIMS separation region 175 with high velocity. This high velocity gas flow causes the gas stream (including a significant portion of the ions) to impinge onto the portion of the inner electrode 165 that directly faces the inlet orifice 150 prior to turning into the analyzer gap, thus discharging a significant percentage of the ion population of interest on the inner electrode. An angular gas stream flowing out of the entrance plate and into the source region may also skew and misalign the ion beam with FAIMS entrance, thereby partially steering the ion beam onto the entrance plate causing further ion loss.

Figure 2:
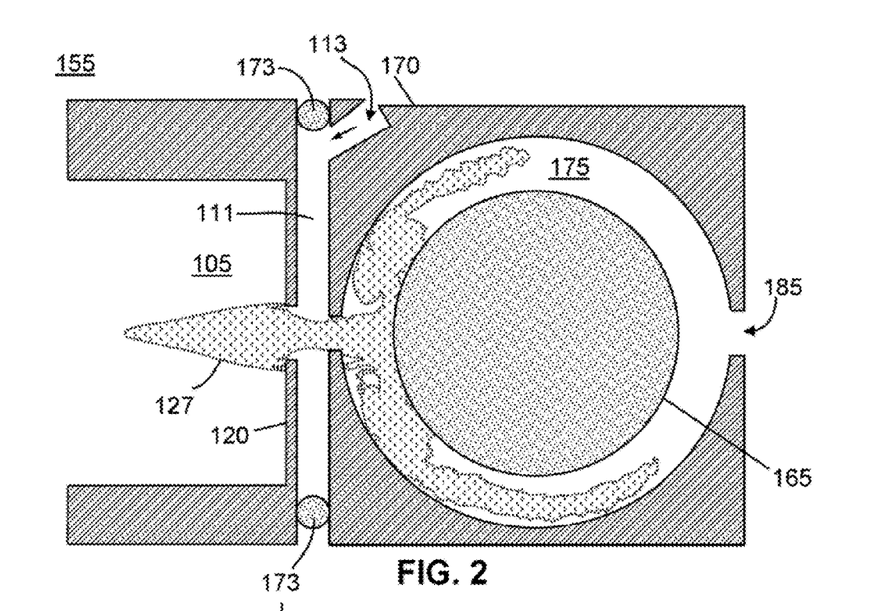
FIG. 2 shows a simulation of a region of ion flow from an ion source region into and through a standard-configuration side-to-side FAIMS apparatus similar to that depicted in FIG. 1.
Figure 3:
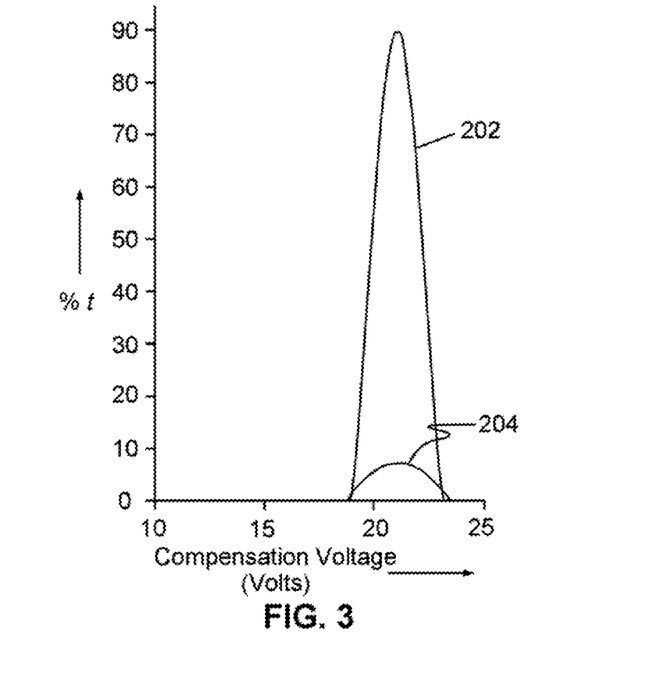
FIG. 3 illustrates a simulated CV scan of bromochloroacetate (BCA) anion through the FAIMS apparatus of FIG. 2, in comparison to a second simulation in which ions are hypothetically introduced between the FAIMS electrodes.

The computational and experimental studies reveal poor ion transmission from the ion source to the exit of FAIMS, e.g. a transmission of approximately 10% for bromochloroacetate anion [BCA, having a mass-to-charge ratio, m/z, of 173]. For example, FIG. 2 shows the results of calculated simulations of ion trajectories of the BCA anion within the FAIMS 155, with the ion-cloud region 127 indicating the region within which most of the ions flow. The simulations shown in FIG. 2, which include simulations of ion flow within a flowing gas, indicate that significant ion losses occur at the entrance plate 120 and on a portion of the inner electrode 165 that is exposed to the FAIMS inlet 150. Curve 204 of FIG. 3 illustrates the results of a simulated CV scan of the BCA anion through the known FAIMS apparatus of FIG. 2. This may be compared with curve 202, which presents the results of a second simulation in which ions are hypothetically introduced between the FAIMS electrodes, without encountering the entrance plate. The overall transmission of ions from the ion source to the exit orifice is only approximately 10%. Although ions are lost near the FAIMS entrance, few ions are lost inside the analytical gap 175 because, owing to the cylindrical shape of the FAIMS electrode (FIG. 1), ions within the separation region 175 that is away from the inlet orifice 150 experience a non-uniform electric field which causes spatial focusing of ions that are travelling in the gap. This ion focusing results in only minimal ion loss of the selected ion species during transport as a result of diffusion or the separation field. In accordance with the above considerations, there is a need in the art of ion transport and analysis for improved means for controlling the effects of gas flow on ion trajectories.

SUMMARY

In a first aspect of the present teachings, a dual gas inlet is provided to maintain a pressure balance in a FAIMS apparatus. Such a dual gas inlet generates symmetrical flows inside the FAIMS gap as well as in an associated ion source region. In a related aspect, a new design of electrode assembly is proposed to facilitate a gentle flow of gas around the FAIMS entrance.

In another aspect in accordance with the present teachings, a novel gas and ion orifice structure is provided for electrodes. The novel orifice structure applies the principles of the Coandă effect, which is the general tendency of a fluid jet to be drawn towards and follow the contour of a curved solid surface. When used as a gas and ion inlet of a FAIMS outer electrode, the novel orifice structure produces curved streamlines of a carrier gas flow such that the gas stream enters a FAIMS gap with a progressive turn away from the inner electrode so as to flow generally parallel to the inner walls of the outer electrode. The orifice is constructed such that the edges of the outer electrode orifice are smoothly curved such that the inner diameter of the orifice increases towards both extremities of the orifice. A gas stream flowing against this curvature will adhere closely to the surface and gradually flow along the curvature. When this curvature is incorporated into the electrode geometry, the gas stream entering the FAIMS will flow gently inside the analyzer gap rather than impact the inner electrode.

In various embodiments, a High Field Asymmetric Waveform Ion Mobility Spectrometry (FAIMS) apparatus is provided, the apparatus comprising: (a) an ion source; (b) a first and a second gas inlet; (c) an expansion chamber receiving first and second gas flows from the first and second gas inlets, respectively; (d) an outer electrode having a generally concave inner surface and comprising: (i) an ion inlet operable to receive ions from the ion source and to receive a combined gas flow comprising portions of the first and second gas flows from the expansion chamber; and (ii) an ion outlet; and (e) an inner electrode having a generally convex outer surface that is disposed in a spaced-apart and facing arrangement relative to the inner surface of the outer electrode for defining an ion separation region therebetween, wherein the combined gas flow and a portion of the ions are received into the ion separation region from the ion inlet and travel through the ion separation region from the ion inlet to the ion outlet.

In various embodiments, a High Field Asymmetric Waveform Ion Mobility Spectrometry (FAIMS) apparatus is provided, the apparatus comprising: (a) an expansion chamber receiving ions from an ion source and a gas flow from a gas inlet; (b) an outer electrode having a generally concave inner surface and comprising: (i) an ion inlet orifice operable to receive ions from the ion source and a portion of the gas flow from the expansion chamber, the ion inlet orifice comprising an orifice wall, an orifice inlet end and an orifice outlet end, the orifice wall being convexly curved between the inlet end and the outlet end; and (ii) an ion outlet; and (c) an inner electrode having a generally convex outer surface that is disposed in a spaced-apart and facing arrangement relative to the inner surface of the outer electrode for defining an ion separation region therebetween, wherein the combined gas flow and a portion of the ions are received into the ion separation region from the ion inlet and travel through the ion separation region from the ion inlet to the ion outlet.

In various other embodiments, A High Field Asymmetric Waveform Ion Mobility Spectrometry (FAIMS) apparatus is provided, the apparatus comprising: (a) an ion source; (b) at least one gas inlet; (c) an expansion chamber receiving ions from the ion source and a gas flow from the at least one gas inlet; (d) a first electrode having a convexly curved surface; and (e) a second electrode have a concavely curved surface that is disposed in a spaced-apart and facing arrangement relative to the convexly curved surface of the first electrode for defining an ion separation region therebetween, the ion separation region receiving the ions and a portion of the gas flow from the expansion chamber, wherein a deflection of an average ion trajectory upon entering the ion separation region is greater than zero degrees but substantially less then ninety degrees.

BRIEF DESCRIPTION OF THE DRAWINGS

The above noted and various other aspects of the present invention will become apparent from the following description which is given by way of non-limiting example only and with reference to the accompanying drawings, not drawn to scale, in which.

DETAILED DESCRIPTION OF EMBODIMENTS

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 1-9, taken in conjunction with the following description.

Figure 4:
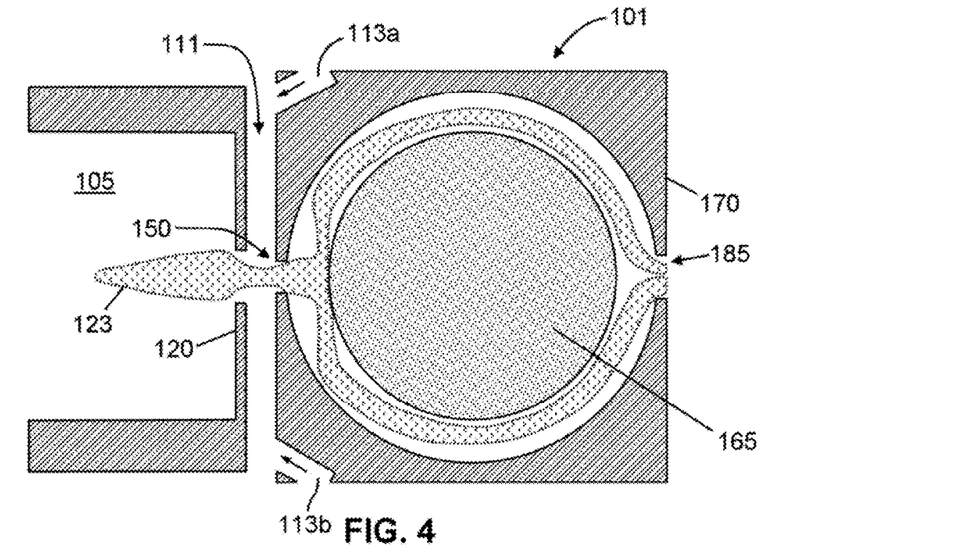
FIG. 4 shows a simulation of a region of ion flow from an ion source region into and through a side-to-side FAIMS apparatus having novel dual gas inlets in accordance with the present teachings.

FIG. 4 schematically illustrates an embodiment of a FAIMS apparatus in that represents a first modification of the apparatus shown in FIGS. 1-2. In contrast the single gas conduit 113 employed in the FAIMS apparatus 155 (FIG. 1), the FAIMS apparatus 101 (FIG. 4) employs two gas conduits 113a, 113b that simultaneously deliver gas flows to the expansion chamber 111 and that are symmetrically disposed about the inlet orifice 150. This symmetric gas introduction within the apparatus 101 eliminates the tendency within the conventional apparatus for a portion of the ions to be pushed, by gas flow from the single conduit 113, towards one side of the apparatus midline. The results of the combined electrostatic and fluid dynamic modeling, which are indicated as ion cloud 123, show a symmetrical flow of ions from source to FAIMS inlet with little or no loss on the entrance plate 120. It is here noted that all fluid dynamic computations referenced in this document were performed using COMSOL Multiphysics® engineering simulation software which is commercially available from COMSOL, Inc., 10850 Wilshire Boulevard, Suite 800 Los Angeles, Calif. 90024 USA. Electric fields and charged particle trajectories were calculated using SIMION® charged particle optics simulation software commercially available from Scientific Instrument Services of 1027 Old York Rd. Ringoes N.J. 08551-1054 USA. Combined fluid dynamic and ion trajectory computations were performed by first calculating bulk gas flows using the COMSOL Multiphysics® software and then inputting the results into a collision model within the SIMION® package.

Even though loss of ions to the entrance plate is minimized within the apparatus 101 (FIG. 4), a non-trivial proportion of ions are still lost by neutralization at the ion inlet orifice of the outer electrode 170 and at a portion of the inner electrode 165 that faces the ion inlet orifice. Computational fluid dynamics calculations indicate that the use of two gas inlet conduits in the configuration shown in FIG. 4 increases the velocity of the gas stream entering the analytical gap and thus accelerates the ions. The excessive ion speed causes collision with the inner electrode resulting in low ion transmission through the apparatus 101.

Figure 5:
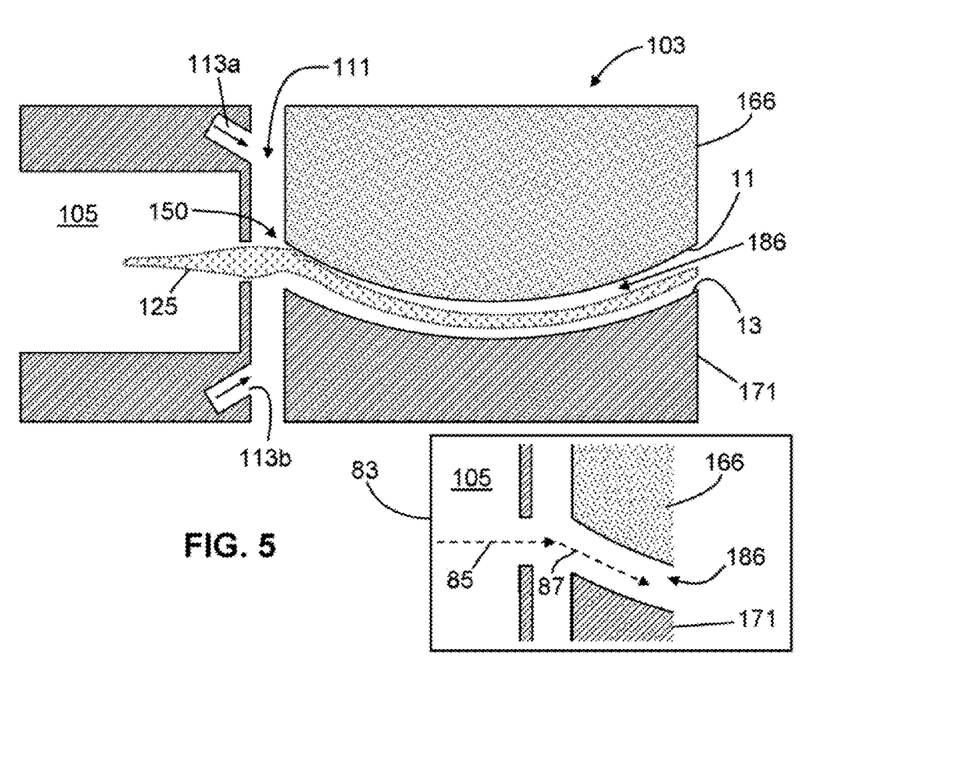
FIG. 5 shows a simulation of a region of ion flow from an ion source region into and through a side-to-side FAIMS apparatus having a novel FAIMS electrode assembly in accordance with the present teachings.

Further design modifications are illustrated in FIG. 5 so as to further reduce ion loss near the FAIMS entrance. Accordingly, the FAIMS apparatus 103 illustrated in FIG. 5 represents a further improvement relative to the FAIMS apparatus 101 of FIG. 4. In both the conventional side-to-side FAIMS apparatus 155 (FIGS. 1-2) as well as the apparatus 101 (FIG. 4), the cylindrical symmetry dictated by the use of an inner electrode 165 comprising a cylinder with circular cross section causes both the carrier gas and the ions of interest to diverge to two different pathways after passing through the ion inlet orifice 150. The geometry is such that a non-trivial proportion of ions are neutralized against the inner electrode 165. The FAIMS apparatus 103 shown in FIG. 5 partially overcomes this problem by replacing the inner electrode 165 and outer electrode 170 by a first electrode 166 and a second electrode 171, respectively, wherein the first electrode 166 has a convexly curved surface 11 and the second electrode 171 has a concavely curved surface 13. The first and second electrodes are disposed such that the surfaces 11, 13 are arranged in a spaced-apart facing arrangement so as to define an annular channel 186 between the surfaces. The FAIMS apparatus 103 retains the two gas conduits 113a, 113b as previously described. However, the inventors have determined that performance is improved if the gas conduits deliver gas flow into the expansion chamber 111 with a flow component in the same direction as the flow of ions or, in other words, with the gas conduits delivering gas from the ion source side of the expansion chamber as shown in FIG. 5.

When a dispersion voltage (DV) and compensation voltage (CV) are applied to at least one of the first and second electrodes 166, 171 of the FAIMS apparatus 103, the annular channel 186 then serves as an analytical gap, as is well-known with regard to the conventional side-to-side FAIMS 155 shown in FIG. 1 as well as with regard to other known FAIMS apparatus designs. However, because the FAIMS 103 does not comprise a cylindrical inner electrode and comprises only a single analytical gap 186, the gas and ion flow, as indicated by the ion cloud 125, does not separate into diverging pathways, as occurs for conventional side-to-side FAIMS apparatuses.

The geometry of the electrode surfaces 11, 13 of the FAIMS apparatus 103 are such that, upon entering the analytical gap 186, the average flow of ions is in a direction that is not directly toward and not perpendicular to either of the surfaces 11, 13 defining the channel 186. Instead, the geometry is such that the inlet orifice 150 into the channel 186 intersects the expansion chamber 111 at an angle such that the average flow direction of ions changes by substantially less than ninety degrees upon their entrance into the channel. This is illustrated in inset 83 of FIG. 5 which shows an enlarged portion of the FAIMS apparatus 103. In the inset, the average or overall trajectory of ions passing into the expansion chamber 111 towards the two electrodes is shown as trajectory 85, whereas the average ion trajectory upon entering the channel (analytical gap) 185 is shown as trajectory 87. The angle of deflection of average ion trajectory is thus greater than zero degrees but substantially less then ninety degrees. As a result, the combined electrostatic and fluid dynamic simulation shows very little ion loss to either electrode, thus suggesting that the novel FAIMS design illustrated in FIG. 5 delivers ions into the FAIMS gap 186 with high efficiency.

Figure 6:
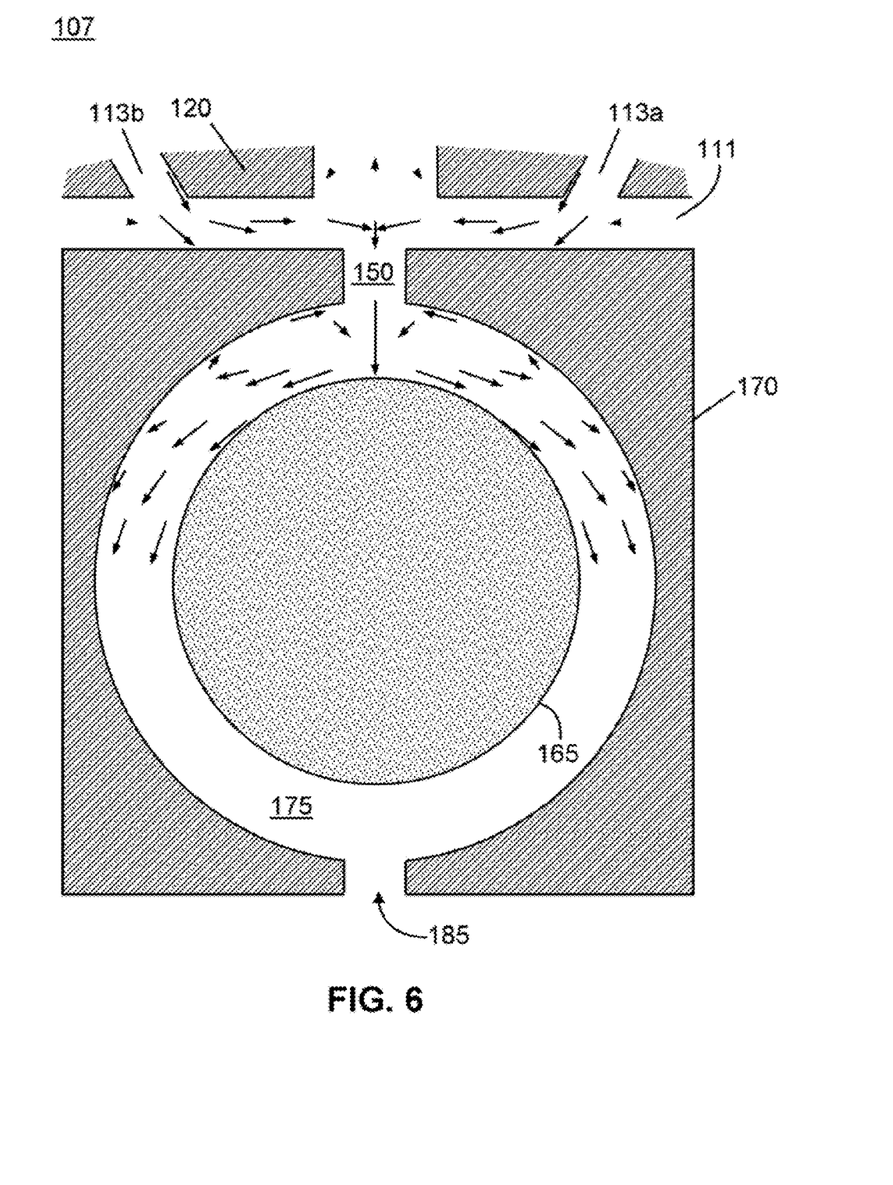
FIG. 6 illustrates gas flow streamlines, as modeled by computational fluid dynamics, through flow channels of a FAIMS apparatus in accordance with the present teachings.

FIG. 6 provides another schematic cross-sectional view of a dual-gas-inlet FAIMS apparatus 107, somewhat similar to the apparatus previously illustrated in FIG. 4. One difference between the apparatus 107 shown in FIG. 6 and the apparatus 101 shown in FIG. 4 is that, in the FAIMS the apparatus 107, the entry of gas into the expansion chamber 111 from the gas conduits 113a, 113b is directed from the entrance-plate side (or, equivalently, from the ion-source side) of the expansion chamber instead of from the side that is opposite to the entrance plate. Inletting the gas in the fashion shown in FIG. 6 reduces the degree of gas counter-flow into the ion source region, thus producing greater flow of carrier gas into the analytical gap 175. In FIG. 6, several flow vectors are provided so as to indicate calculated gas flow within the ion expansion chamber 111 and the analytical gap 175. These vectors indicate only gas flow, as calculated from fluid dynamics principles, and do not incorporate ion movement. The ion inlet orifice 150 is indicated in FIG. 6 as a simple cylindrical bore hole through the outer electrode 170. This shape of the ion inlet orifice shown in FIG. 6 is similar to its shape in the conventional side-to-side FAIMS apparatus 155 (FIG. 1). The resulting flow profile is high velocity and aligned directly onto the inner electrode 165 where this electrode faces the ion inlet orifice 150. Experimental data also show this phenomenon in the form of a buildup of chemical material on the inner electrode. The fluid dynamics calculations graphically illustrated in FIG. 6 also indicate the existence of some degree of recirculation flow within the analytical gap on either side of the ion inlet orifice 150. Such recirculation could possibly cause unwanted neutralization of ions on both inner and outer electrodes.

Figure 7:
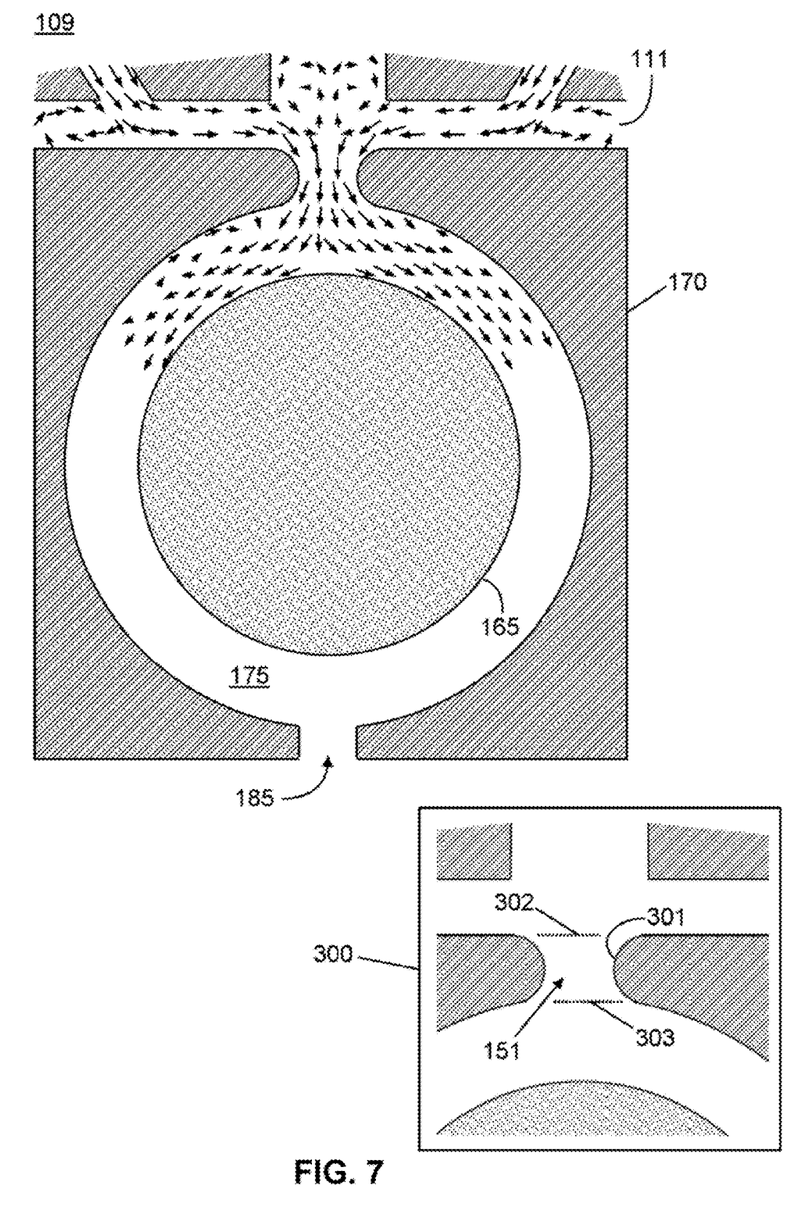
FIG. 7 illustrates gas flow streamlines, as modeled by computational fluid dynamics, through flow channels of a FAIMS apparatus having entrance electrode that is modified so as to exploit the Coandă effect.

FIG. 7 shows the FAIMS gas flow into an electrode set that is modified so as to decrease the volume and rate of gas flow directly onto the inner electrode. The FAIMS apparatus 109 that is schematically illustrated in FIG. 7 is identical to the FAIMS apparatus 107 shown in FIG. 6 except with regard to the shape of the ion inlet orifice. Inset 300 of FIG. 7 illustrates an enlarged view of the vicinity of the ion inlet orifice 151 of the FAIMS 109. Note that the wall of the ion inlet orifice 151 of the outer electrode as shown in FIG. 7 is slightly enlarged and rounded as compared to the squared off orifice 150 in the conventional electrode set (e.g., FIG. 6). The walls 301 of the ion inlet orifice 151 of the FAIMS apparatus 109 are convexly curved between the orifice inlet end 302 and the orifice outlet end 303. Thus, the inner diameter of the ion inlet orifice is at a minimum value within the orifice. Because of the curvature, the inner diameter smoothly increases or flares outward in both directions (i.e., towards the two ends of the orifice) away from the region of minimum diameter. The gas flow in the vicinity of the rounded walls of the ion inlet orifice 151 demonstrates the so-called Coandă effect, which is the general tendency of a fluid jet to be drawn towards and follow the contour of a curved solid surface. By means of the Coandă effect, the carrier gas flow entering the analytical gap 175 of the FAIMS apparatus 109 (FIG. 7) is kept closer to the curvature of the entrance orifice than would otherwise be the case. This behavior allows for incorporation of the gas stream into the gap and away from the inner electrode as is indicated in FIG. 7 by the smooth divergence of gas flow vectors away from the center electrode 165 and into the analytical gap 175. The smooth divergence of the carrier gas into away from the center electrode and into the analytical gap 175 is expected to urge ions along similar pathways, thereby reducing the proportion of ions that are lost as a result of collision with the center electrode. As indicated by the fluid dynamics calculations, the smooth divergence also leads to a larger zone of laminar flow within the analytical gap, with reduced recirculation flow near the entrance orifice.

Figure 8:
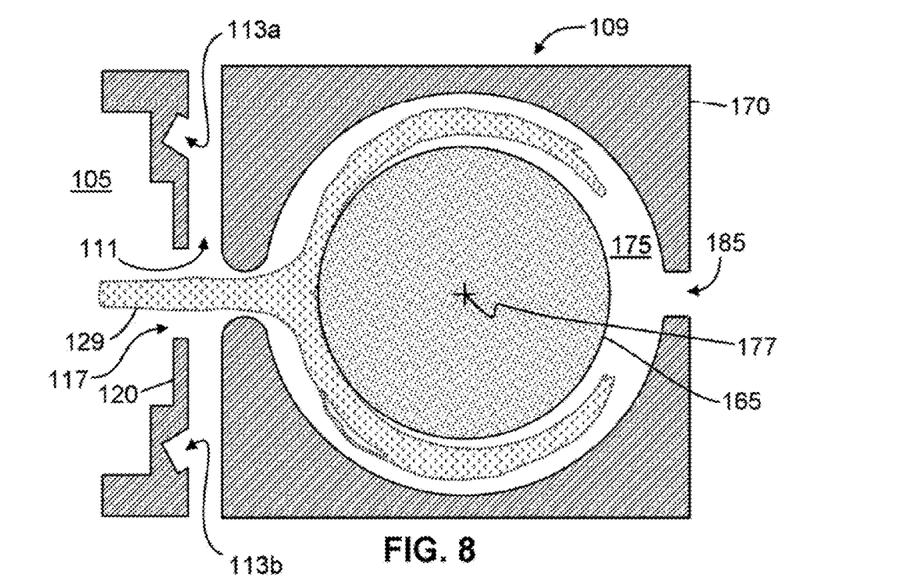
FIG. 8 a simulation of a region of ion flow from an ion source region into and through a side-to-side FAIMS apparatus that is modified so as to exploit the Coandă effect.
Figure 9:
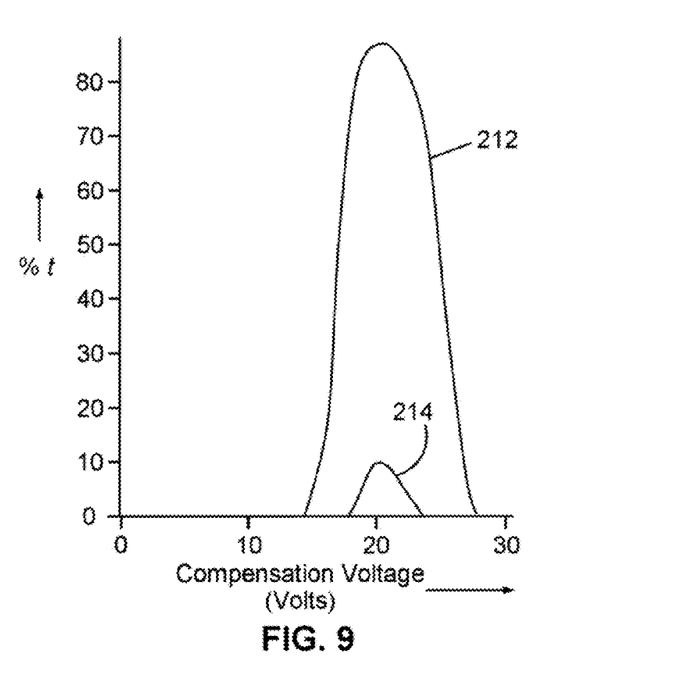
FIG. 9 illustrates a comparison between simulated CV scans corresponding to the FAIMS apparatuses of FIG. 2 and FIG. 8.

FIG. 8 shows the results of combined fluid dynamic and ion trajectory modeling, through the FAIMS apparatus 109. FIG. 9 shows a comparison between the transmission efficiency of the apparatus having the curved an inlet orifice 151 and shown in FIG. 8 (curve 212) with that of the prior FAIMS apparatus shown in FIGS. 1 and 2 (curve 214). It is evident from the shape of the ion cloud 129 in FIG. 8 that the curved orifice design promotes a smoother bifurcation of ion flow prior around the center electrode and into the analytic gap then is indicated for non-curved orifice designs. The smoother flow bifurcation appears to have the effect of reducing gas recirculation flow with the analytical gap just after passing through the inlet orifice, thereby significantly reducing ion neutralization at both inner and outer electrodes (for example, compare FIG. 8 with FIG. 1).

It should be noted that, in addition to the provision of a curved inlet orifice, the design of the FAIMS apparatus 109 illustrated in FIG. 8 further differs from the design of the known FAIMS apparatus (FIG. 1) through the provision of a wider aperture 117 in the entrance plate 120 as well as through slight widening of the inlet ion orifice 151 (measured at its point of minimum width). Specifically, the width of the entrance plate aperture 117 is approximately 60% greater in the FAIMS 109 and the width of the ion inlet orifice (measured at its minimum diameter) is approximately 26% greater than the respective aperture widths in the known FAIMS apparatus 155 (FIGS. 1 and 2). These wider apertures are such as to maintain the width of the ion cloud 129 at its region of passage through the ion inlet orifice of the novel FAIMS 109 (FIG. 8) the same as its width at its region of passage through the ion inlet orifice of the known FAIMS (FIG. 2) in which it nearly completely fills the orifice.

The simple re-design of the cross-sectional shape of the ion inlet orifice—as indicated by comparison of FIG. 7 with FIG. 6-*improves* the uniformity of flow of carrier gas through the FAIMS apparatus. This smoother flow is such that there is highly reduced flow rate of the carrier gas (and entrained ions) directly onto the electrodes, relative to the conventional FAIMS apparatus 155 (FIG. 2). This smoother flow is believed to have a major effect in yielding the results of FIG. 9, in which simulated CV scans through the FAIMS 109 and through the FAIMS 155 are shown as curves 212 and 214, respectively. The calculated approximate 10-fold improvement in transmission is achieved with minimal re-design of the overall apparatus dimensions or shape, relative to the conventional side-to-side FAIMS. In some implementations, this simple modification of an existing FAIMS design may be more desirable than using a different form of FAIMS apparatus, such as the apparatus 103 of FIG. 5.

Figure 10A:
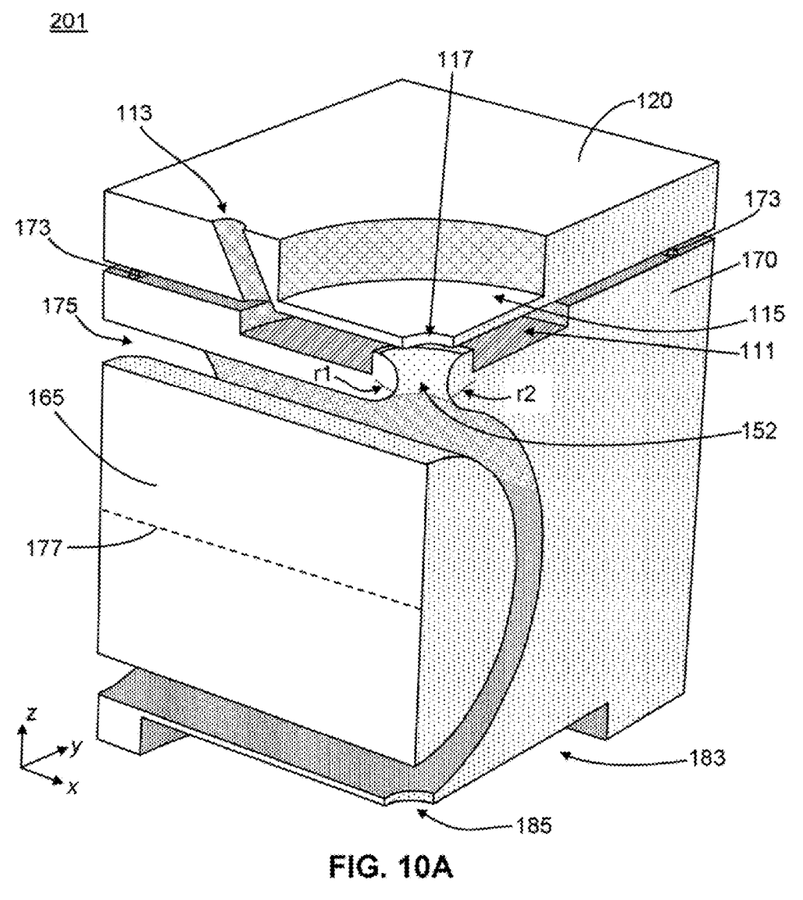
FIG. 10A illustrates a doubly-cutaway perspective view of another FAIMS apparatus in accordance with the present teachings.
Figure 10B:
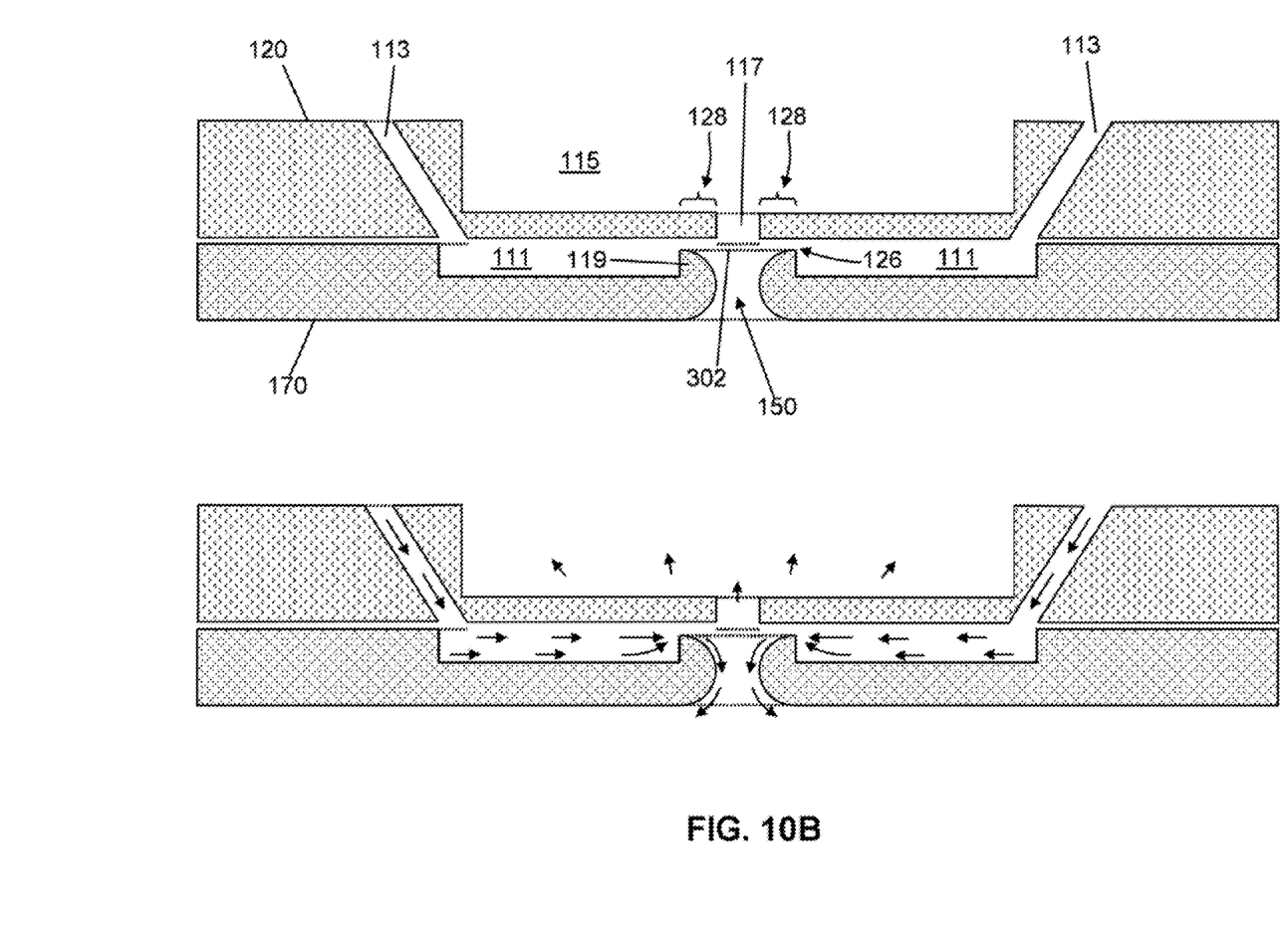
FIG. 10B illustrates a cross-section view (both upper and lower diagrams) of the entrance plate and a portion of the outer electrode of the FAIMS apparatus of FIG. 10A and schematically illustrates flow vectors (lower diagram) within the gas expansion chamber of the apparatus.

FIG. 10A illustrates a perspective sectional view (a quarter section view) of another FAIMS apparatus 201 in accordance with the present teachings. The illustration in this figure is doubly-cutaway view that is cut away in a plane (the x-z plane) that includes the cylindrical axis 177 of the FAIMS inner electrode 165 and is also cut away in a plane (the y-z plane) that is perpendicular to the cylindrical axis 177. Each such sectional plane bisects the overall FAIMS apparatus 201 and, thus, the view shown in FIG. 10A is a quarter-section view. FIG. 10B illustrates a cross-section view (both upper and lower diagrams of FIG. 10B) of the entrance plate and a portion of the outer electrode of the FAIMS apparatus of FIG. 10A. FIG. 10B also schematically illustrates (lower diagram only) flow vectors within the gas expansion chamber 111 of the apparatus 201.

Many of the elements of the FAIMS apparatus 201 are similar to corresponding elements in other FAIMS apparatuses previously described herein. However, the FAIMS apparatus 201 differs from previously-described apparatus with regard to the configuration of the ion inlet orifice 152, the gas expansion chamber 111 and the relationship between the inlet orifice 152 and the gas expansion chamber 111. As shown, the apparatus 201 also includes a desolvation chamber 115 recessed into the entrance plate 120 and surrounding the entrance plate aperture 117.

In contrast to apparatuses previously described herein, the expansion chamber 111 of the apparatus 201 forms a recess within the entrance plate 120 in a fashion so as to circumferentially surround the ion inlet orifice 152. Further, the expansion chamber recess is provided such that the a portion of the walls of the ion inlet orifice 152 protrude into the expansion chamber 111 so as to form a ring 119 that circumferentially surrounds a portion of the ion inlet orifice 152. The space between the entrance plate 120 and the inlet end 302 of the ion inlet orifice comprises a narrow gap 126 between the entrance plate and the inlet end of the ion inlet orifice. The entrance plate 120 is configured such that an overlap portion 128 of a face of the entrance plate that bounds the expansion chamber 111 extends beyond the expansion chamber so as to also face the ring portion 119 of the walls of the ion inlet orifice 152.

As a result of the configuration shown in FIGS. 10A-10B, gas that enters the expansion chamber 111 through gas conduits 113 is caused to flow around the circumference of the ring 119 and then to flow into and through the gap 126. The apparatus 201 is configured such that the width of the gap 126 is significantly less than the width of the expansion chamber 111, wherein the width of the gap is measured between the entrance plate 120 and the inlet end 302 of the ion inlet orifice 152 and the width of the chamber 111 is measured between the facing surfaces of the entrance plate 120 and the outer electrode 170 that bound the chamber. Because of these different widths, the gas pressure and flow velocity are both caused to increase as the gas flows into the gap. The increased-velocity gas flow then enters the inlet end 302 of the ion inlet orifice 152 at through the entirety of the gap 126 that circumferentially surrounds the inlet end of the ion inlet orifice 152. Ions pass through the aperture 117 in the entrance plate and then cross the gap 126 and pass into the ion inlet orifice 152 where they are entrained in the gas flow. The overlap portion 128 of the entrance plate confines the gas to the gap 126 and enables the increase in flow velocity.

As is illustrated in the lower portion of FIG. 10B, the increased gas flow velocity produced by the squeezing of the gas flow into the gap 126 causes a high-velocity boundary layer to form against the convexly curved interior walls of the ion inlet orifice 152, thereby causing the high velocity gas to follow the curved surface of the walls in accordance with the Coanda effect. Thus, as previously discussed in regard to the apparatus 109 shown in FIGS. 7-8, the high velocity gas flow (and, consequently, the majority of the gas itself) is diverted into the analytical gap 175 so as to avoid impacting the inner electrode 165. The majority of the entrained ions are carried along with the gas, thereby improving the ion throughput through the FAIMS apparatus.

The curvature of the interior walls of the ion inlet orifice 152 of the FAIMS apparatus 201 (FIG. 10A) differs from the curvature of the walls of the inlet orifice 151 of the FAIMS apparatus 109 (FIGS. 7-8) in that the walls of the inlet orifice 152 comprise different radii of curvature in different cross sections. In the x-z cross section taken parallel to the cylindrical axis 177 of the inner electrode, the radius of curvature is of the wall is $r_1$ whereas, in the y-z cross section oriented perpendicular to the axis 177, the radius of curvature is $r_2$, where $r_2 > r_1$. The reason for this difference in the wall curvature in different directions is that, in the y-z plane, the required deflection of the gas jet in they direction is greater than the amount of deflection that that is either necessary or desirable in the x-direction in the x-z plane. The greater degree of deflection required in the y-z plane is a simple result of the geometry of the annular analytical gap 175. For example, consider gas that approaches the ion inlet orifice 152 along the negative-y direction in the expansion chamber 111. In order to be completely diverted into the analytical gap 175, the direction of flow must be diverted so as to have a component vector in the positive y-direction. No such requirement exists for gas that approaches the ion inlet orifice 152 along, for example, the positive-x direction in the expansion chamber 111. In this latter case, the most important requirement is to maintain most of the gas flow within the analytical gap near an axis (not shown) that passes from the ion inlet orifice 152 to the ion exit orifice 185. The greater radius $r_2$ in the y-z cross section allows the required greater amount of angular deflection of the gas jet to be accomplished sufficiently gradually such that the boundary layer does not detach from the curved wall.

Figure 11:
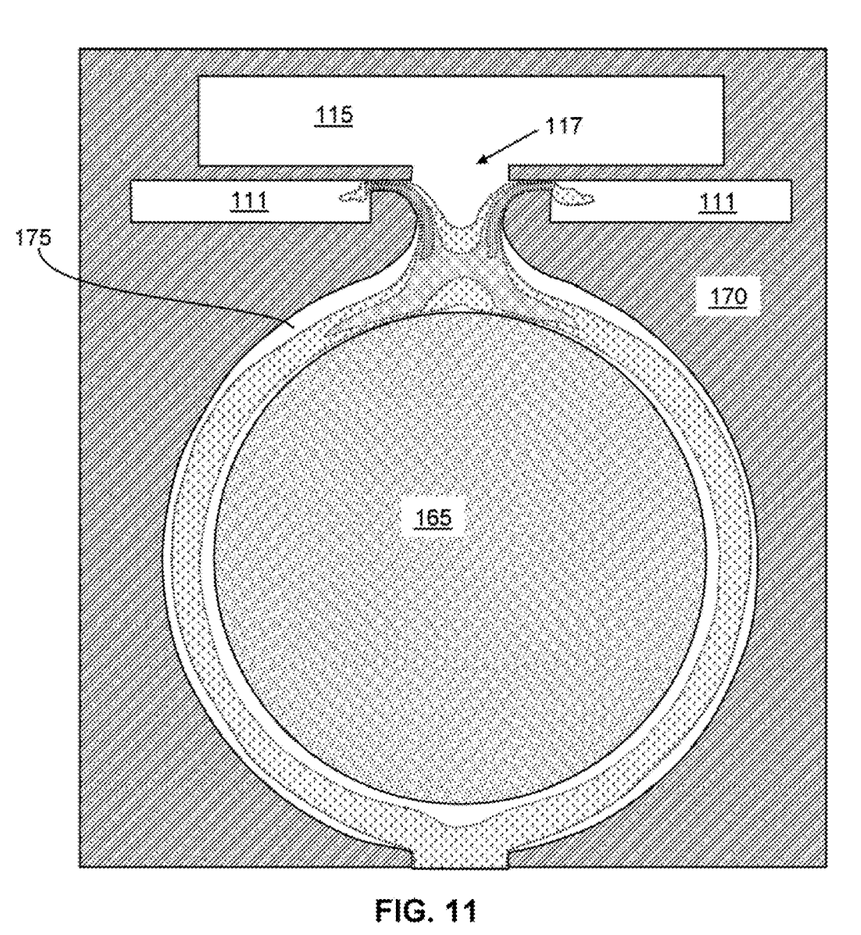
FIG. 11 illustrates a contour plot of calculated gas flow velocities within the FAIMS apparatus of FIG. 10.
Figure 12:
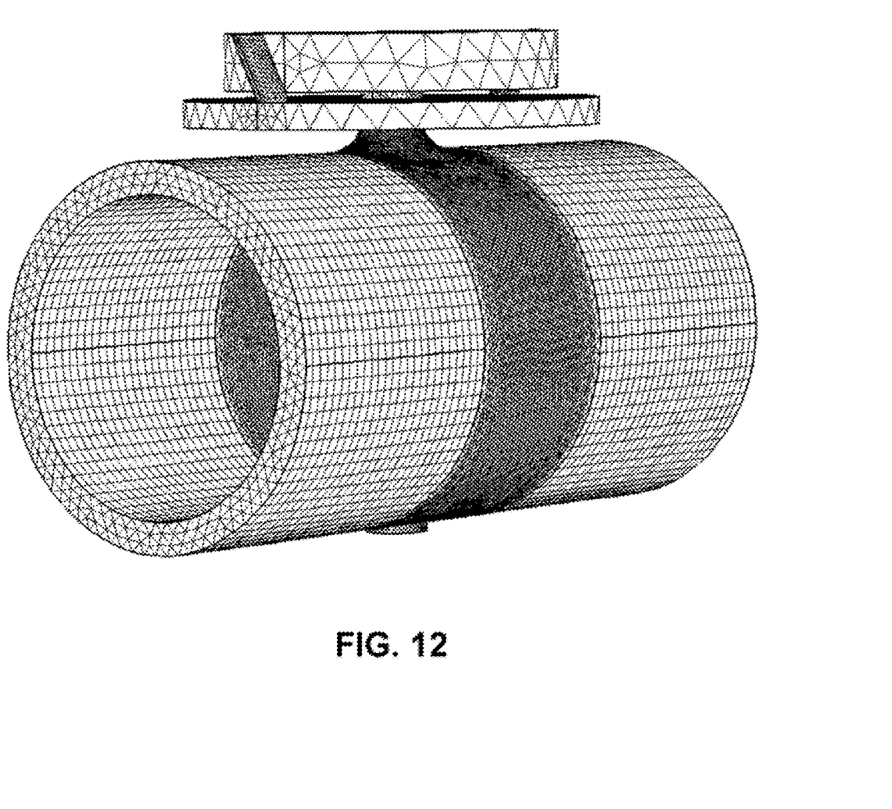
FIG. 12 illustrates a view of the internal gas volume within the FAIMS apparatus of FIG. 10, illustrating a grid of finite elements used in the fluid dynamic computations used to generate the data illustrated in FIG. 11.

FIG. 11 illustrates a contour plot of calculated gas flow velocities within the annular analytical gap 175 of the FAIMS apparatus 201 of FIG. 10, shown along the y-z plane. Regions with progressively greater flow velocities are shown with progressively darker shading. The calculations were performed using a computational fluid dynamics routing employing the finite element grid pattern shown in FIG. 12. The grid pattern in FIG. 12 is superimposed upon the internal gas volume within the FAIMS apparatus of FIG. 10. Note that no apparatus elements are shown in FIG. 12. The grid or mesh spacing is not uniform. A more closely spaced mesh was used in the region around the curved orifice walls and within the vicinity of the axis that passes from the ion inlet orifice to the ion exit orifice so as to accurately model the gas flow in these regions in which the velocity and flow streamlines change rapidly. The average quality of the mesh cells around the curved wall surface was 0.85.

As illustrated in FIG. 1, FAIMS apparatuses are often used in conjunction with mass spectrometers, so as to eliminate interfering background ions from an ion stream prior to mass spectrometry analysis. For practical reasons, there are size limitations to a FAIMS apparatus that is interfaced to a mass spectrometer in such a fashion. From a practical standpoint, the size of the FAIMS apparatus is limited such that the diameter of the inner electrode is limited to approximately 20 mm or less and the width of the analytical gap is limited to approximately 20 mm or less. Accordingly, the fluid dynamic calculations illustrated in the accompanying figures were performed so as to model a FAIMS apparatus within this size range. The fluid dynamics calculations indicate that decreasing the width of the gap 126 (FIG. 10B) yields greater gas jet velocities corresponding to better deflection around the curved inlet orifice walls and better overall throughput. If the gap width is greater than 0.75 mm, then the streamlines diverge and separate from the curved wall surface. However, for practical reasons, the width of the gap is preferably greater than about 0.25 mm. Also, increasing the gas flow rate gives higher throughput, provided that the gas flow does not become turbulent. The Reynolds number for flow in the modeled apparatus is approximately 70 for an internal flow rate of 0.5 m/s and is approximately 209 for an internal flow rate of 5.0 m/s, so the flow remains laminar. However, throughput needs to be balanced against FAIMS analytical resolution, which decreases as the flow rate increases.

The discussion included in this application is intended to serve as a basic description. Although the present invention has been described in accordance with the various embodiments shown and described, one of ordinary skill in the art will readily recognize that there could be variations to the embodiments or combinations of features in the various illustrated embodiments and those variations or combinations of features would be within the spirit and scope of the present invention. The reader should thus be aware that the specific discussion may not explicitly describe all embodiments possible; many alternatives are implicit. As but one example, FIG. 10 illustrates a FAIMS apparatus comprising both an ion inlet orifice 152 that has curved walls and that protrudes into a gas expansion chamber and also comprising multiple gas inlet conduits 113 providing FAIMS bath gas to the expansion chamber from opposing sides. Although both such features are beneficial, the benefits of the novel ion inlet orifice configuration could also be realized using a conventional single gas inlet conduit. As another example, although the FAIMS bath gas is illustrated as being provided through "conduits", any form of gas inlet could suffice, such as for example, gas inlet "apertures". Similarly, although the ion inlet is described herein as an "orifice", it could equally take the form of or be described as an "aperture" or, in some embodiments, a "conduit". Accordingly, many modifications may be made by one of ordinary skill in the art without departing from the scope and essence of the invention. Neither the description nor the terminology is intended to limit the scope of the invention—the invention is defined only by the claims. Any patents, patent applications or other publications mentioned herein are hereby explicitly incorporated herein by reference in their respective entirety.

What is claimed is:

1. A High Field Asymmetric Waveform Ion Mobility Spectrometry (FAIMS) apparatus comprising:
   (a) an ion source;
   (b) a first and a second gas inlet;
   (c) an expansion chamber receiving first and second gas flows from the first and second gas inlets, respectively;
   (d) an outer electrode having a generally concave inner surface and comprising:
      (i) an ion inlet operable to receive ions from the ion source and to receive a combined gas flow comprising portions of the first and second gas flows from the expansion chamber; and
      (ii) an ion outlet; and
   (e) an inner electrode having a generally convex outer surface that is disposed in a spaced-apart and facing arrangement relative to the inner surface of the outer electrode for defining an ion separation region therebetween, wherein the combined gas flow and a portion of the ions are received into the ion separation region from the ion inlet and travel through the ion separation region from the ion inlet to the ion outlet.

2. A FAIMS apparatus as recited in claim 1, wherein the first and second gas inlets are disposed at opposite sides of the ion inlet and are directed towards one another within the expansion chamber.

3. A FAIMS apparatus as recited in claim 2, wherein a portion of the inner electrode comprises a cylinder such that the combined gas flow and the portion of the ions travel from the ion inlet to the ion outlet through the ion separation region along two pathways at opposite sides of the cylinder.

4. A FAIMS apparatus as recited in claim 3, wherein the ion inlet comprises an orifice through the outer electrode having an orifice wall, an orifice inlet end and an orifice outlet end, wherein the orifice wall is convexly curved between the inlet end and the outlet end.

5. A FAIMS apparatus as recited in claim 4, wherein a portion of the orifice wall protrudes into the expansion chamber so as to comprise a ring surrounding the orifice.

6. A FAIMS apparatus as recited in claim 5, further comprising an entrance plate having an aperture through which the ions are provided to the ion inlet orifice, wherein the combined gas flow passes through a gap between a flat surface of the entrance plate and the ring.

7. A FAIMS apparatus as recited in claim 6, wherein a width of the gap is within the range 0.25 mm to 0.75 mm.

8. A FAIMS apparatus as recited in claim 4, wherein the curvature comprises different radii of curvature along different cross sections of the ion inlet orifice.

9. A High Field Asymmetric Waveform Ion Mobility Spectrometry (FAIMS) apparatus comprising:
   (a) an expansion chamber receiving ions from an ion source and a gas flow from one or more gas inlets;
   (b) an outer electrode having a generally concave inner surface and comprising:
      (i) an ion inlet orifice operable to receive the ions and a portion of the gas flow from the expansion chamber, the ion inlet orifice comprising an orifice wall, an orifice inlet end and an orifice outlet end, the orifice wall being convexly curved between the orifice inlet end and the orifice outlet end; and
      (ii) an ion outlet; and
   (c) an inner electrode having a generally convex outer surface that is disposed in a spaced-apart and facing arrangement relative to the inner surface of the outer electrode for defining an ion separation region therebetween, wherein the portion of the gas flow and a portion of the ions are received into the ion separation region from the ion inlet orifice and travel through the ion separation region from the ion inlet orifice to the ion outlet.

10. A FAIMS apparatus as recited in claim 9, wherein a portion of the inner electrode comprises a cylinder such that the portion of the gas flow and the portion of the ions travel from the ion inlet orifice to the ion outlet through the ion separation region along two pathways at opposite sides of the cylinder.

11. A FAIMS apparatus as recited in claim 9, wherein a portion of the orifice wall protrudes into the expansion chamber so as to comprise a ring surrounding the ion inlet orifice.

12. A FAIMS apparatus as recited in claim 1 further comprising an entrance plate having an aperture through which the ions are provided to the ion inlet orifice, wherein the portion of the gas flow passes through a gap between a flat surface of the entrance plate and the ring.

13. A FAIMS apparatus as recited in claim 12, wherein a width of the gap is within the range 0.25 mm to 0.75 mm.

14. A FAIMS apparatus as recited in claim 9, wherein the curvature comprises different radii of curvature along different cross sections of the ion inlet orifice.

15. A High Field Asymmetric Waveform Ion Mobility Spectrometry (FAIMS) apparatus comprising:
(a) an ion source;
(b) at least one gas inlet;
(c) an expansion chamber receiving ions from the ion source and a gas flow from the at least one gas inlet;
(d) a first electrode having a convexly curved surface; and
(e) a second electrode have a concavely curved surface that is disposed in a spaced-apart and facing arrangement relative to the convexly curved surface of the first electrode for defining an ion separation region therebetween, the ion separation region receiving the ions and a portion of the gas flow from the expansion chamber, wherein a deflection of an average ion trajectory upon entering the ion separation region is greater than zero degrees but substantially less then ninety degrees.

* * * * *